(12) United States Patent
Hulse et al.

(10) Patent No.: US 8,653,311 B2
(45) Date of Patent: Feb. 18, 2014

(54) AZEOTROPE-LIKE COMPOSITION OF HEXAFLUOROPROPANE, HEXAFLUOROPROPENE AND HYDROGEN FLUORIDE

(71) Applicant: Honeywell International Inc., Morristown, NJ (US)

(72) Inventors: Ryan Hulse, Getzville, NY (US); Hang T. Pham, Amherst, NY (US); Rajiv R. Singh, Getzville, NY (US); Hsueh S. Tung, Getzville, NY (US); Daniel C. Merkel, Orchard Park, NY (US); Konstantin A. Pokrovski, Orchard Park, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/860,644

(22) Filed: Apr. 11, 2013

(65) Prior Publication Data
US 2013/0217929 A1   Aug. 22, 2013

Related U.S. Application Data

(62) Division of application No. 12/788,885, filed on May 27, 2010, now Pat. No. 8,436,218.

(51) Int. Cl.
*C07C 17/02* (2006.01)
*C07C 17/04* (2006.01)

(52) U.S. Cl.
USPC .......................................... 570/164; 570/165

(58) Field of Classification Search
USPC ................................ 570/164, 165
See application file for complete search history.

(56) References Cited

U.S. PATENT DOCUMENTS

| 5,563,304 A | 10/1996 | Rao et al. |
| 6,388,147 B1 | 5/2002 | Rao et al. |
| 6,407,297 B1 | 6/2002 | Ewing |
| 6,677,493 B1 | 1/2004 | Miller et al. |
| 6,900,362 B2 | 5/2005 | Miller et al. |
| 7,183,448 B2 * | 2/2007 | Nakada et al. ................. 570/164 |
| 2001/0004961 A1 | 6/2001 | Herkelmann et al. |
| 2001/0054705 A1 | 12/2001 | Felix et al. |
| 2003/0164283 A1 | 9/2003 | Brandstater et al. |
| 2007/0112229 A1 | 5/2007 | Mukhopadhyay et al. |
| 2007/0197842 A1 | 8/2007 | Mukhopadhyay et al. |
| 2008/0051612 A1 | 2/2008 | Knapp et al. |
| 2009/0124837 A1 | 5/2009 | Mukhopadhyay et al. |
| 2009/0234165 A1 | 9/2009 | Chiu et al. |
| 2009/0240090 A1 | 9/2009 | Merkel et al. |
| 2009/0287026 A1 | 11/2009 | Kopkalli et al. |

FOREIGN PATENT DOCUMENTS

| EP | 1084093 A1 | 3/2001 |
| WO | 2008024508 A1 | 2/2008 |

OTHER PUBLICATIONS

Kim, et al., "A Study to Determine the Existence of an Azeotropic R-22 "Drop-In" Substitute," prepared by U.S. Department of Commerce for Electric Power Research Institute, Mar. 1996, pp. 1-45, U.S.

Morrison, et al, "Azeotropy in Refrigerant Mixtures," International Journal of Refrigeration, 1993, pp. 129-138, vol. 16, No. 2. U.S.

* cited by examiner

*Primary Examiner* — Shawquia Young
(74) *Attorney, Agent, or Firm* — Bruce O. Bradford

(57) ABSTRACT

The present invention relates to an azeotropic or azeotrope-like mixture consisting essentially of 1,1,1,2,3,3-hexafluoropropane, hexafluoropropene and hydrogen fluoride.

11 Claims, No Drawings

AZEOTROPE-LIKE COMPOSITION OF HEXAFLUOROPROPANE, HEXAFLUOROPROPENE AND HYDROGEN FLUORIDE

CROSS REFERENCES TO RELATED APPLICATIONS

The present invention is a divisional of U.S. application Ser. No. 12/788,885 (now U.S. Pat. No. 8,436,218), the contents of which are incorporated by reference herein in its entirety.

FIELD OF THE INVENTION

The present invention pertains to azeotropic and azeotrope-like compositions. More particularly, the present invention relates to ternary azeotrope-like compositions of hydrohalocarbons and hydrogen fluoride.

BACKGROUND OF THE INVENTION

Chlorofluorocarbons (CFCs) like trichlorofluoromethane and dichlorodifluoromethane have been traditionally used as refrigerants, blowing agents and diluents for gaseous sterilization. In recent years, there has been universal concern that completely halogenated chlorofluorocarbons might be detrimental to the Earth's ozone layer. Therefore, stratospherically safer alternatives to these materials are desirable.

There is presently a worldwide effort to use fluorine-substituted hydrocarbons which contain fewer or no chlorine substituents. The production of HFCs, i.e. compounds containing only carbon, hydrogen and fluorine, has been the subject of interest to provide environmentally desirable products that could provide a substitute to CFCs. Such compounds are known in the art to be produced by reacting hydrogen fluoride with various hydrochlorocarbon compounds. While HFCs are considered to be much more environmentally advantageous than hydrochlorofluorocarbons (HCFCs) or chlorofluorocarbons (CFCs) because they are not non-ozone depleting, recent data indicates that they may also contribute to greenhouse global warming. Accordingly, alternatives to HFCs, HCFCs, and CFCs are also being explored.

Hydrofluoroolefins ("HFOs") present one possibility as replacements because they exhibit low ozone depletion potential and contribute little to greenhouse global warming. One such HFO is 2,3,3,3-tetrafluoropropene (HFO-1234yf), which has been well characterized as effective refrigerant, heat transfer medium, propellant, foaming agent, blowing agent, gaseous dielectric, sterilant carrier, polymerization medium, particulate removal fluid, carrier fluid, buffing abrasive agent, displacement drying agent and power cycle working fluid. It may be produced by a number of different methods including those described within U.S. Patent Application Nos. 20070197842, 20070112229, 20090124837, 20090287026, 20090240090, and 20090234165, the contents of which are incorporated herein by reference.

U.S. Patent Application No. 20090234165, in particular, discloses the formation of 1,1,1,2,3,3-hexafluoropropane (HFC-236ea) as an intermediate in the production of 2,3,3,3-tetrafluoropropene (HFO-1234yf). One drawback to this reaction, however, is that impurities present throughout the reaction process (e.g. catalysts, reaction by-products, process starting materials, and the like) interfere with the isolation and conversion of HFC-236ea. Halocarbon reactant or by-product impurities that are particularly problematic include, but not limited to, 1,1,1,2,3-pentafluoropropane, 1,1,3,3-pentafluoropropane, 1,1,1,2-tetrafluoropropane, 1,1,1,3-tetrafluoropropane, (E)1,2,3,3,3-pentafluoropropene, (Z)1,2,3,3,3-pentafluoropropene, 3,3,3-trifluoropropene, 1,1,1-trifluoropropane, 3,3,3-trifluoropropyne, (Z)1,3,3,3-tetrafluoropropene, and (E)1,3,3,3-tetrafluoropropene. Accordingly, methods for isolation/purification of HFC-236ea from such compounds are desirable.

It is generally known that azeotrope and azeotrope-like compositions provide good mechanisms for product purification. Of particular interest are mixtures containing hydrofluorocarbons and hydrogen fluoride, which are useful in the preparation and/or purification of desirable hydrofluorocarbons and chlorofluoroolefin products. The identification of such compositions is difficult, however, because of the relative unpredictability of azeotrope formation. Therefore, industry is continually seeking new HFO-based mixtures that are acceptable and/or may be used to produce HFOs or HFO-based mixtures that are environmentally safer substitutes for existing CFCs, HCFCs, and HFCs.

This invention satisfies these needs among others.

SUMMARY OF THE INVENTION

In one embodiment, the instant invention relates to an azeotropic or azeotrope-like composition consisting essentially of 1,1,1,2,3,3-hexafluoropropane (HFC-236ea), hexafluoropropene (HFP) and hydrogen fluoride (HF). The azeotropic or azeotrope-like composition includes from about 1 to about 10 wt % hydrogen fluoride, from about 1 to about 10 wt % hexafluoropropene, and from about 80 to about 98 wt % of 1,1,1,2,3,3-hexafluoropropane, based on the total weight of the azeotropic or azeotrope-like composition, and has a boiling point of about from 0° C. to about 60° C. at a pressure of about 17 psia to about 125 psia. In further embodiments, the azeotropic or azeotrope-like composition has from about 1.5 to about 8.4 wt % hydrogen fluoride, from about 3.5 to about 4.9 wt % hexafluoropropene, and from about 88.1 to about 93.6 wt % of 1,1,1,2,3,3-hexafluoropropane, based on the total weight of the azeotropic or azeotrope-like composition, and has a boiling point of about 0° C. at a pressure of about 17±3 psia, about 25° C. at a pressure of about 44±5 psia, or about 60° C. at a pressure of about 123±5 psia.

In non-limiting embodiments, the azeotropic or azeotrope-like composition has from about 1 to about 10 wt % hydrogen fluoride, from about 1 to about 10 wt % hexafluoropropene, and from about 80 to about 98 wt % of 1,1,1,2,3,3-hexafluoropropane, and has a boiling point of about 0° C. at a pressure of about 17±3 psia. In further non-limiting embodiments, the azeotropic or azeotrope-like composition has from about 1.5 to about 10 wt % hydrogen fluoride, from about 1 to about 10 wt % hexafluoropropene, and from about 80 to about 98 wt % of 1,1,1,2,3,3-hexafluoropropane and has a boiling point of about 25° C. at a pressure of about 44±5 psia. In even further non-limiting embodiments, the azeotropic or azeotrope-like composition has from about 2 to about 10 wt % hydrogen fluoride, from about 1 to about 10 wt % hexafluoropropene, and from about 80 to about 98 wt % of 1,1,1,2,3,3-hexafluoropropane and has a boiling point of about 60° C. at a pressure of about 123±5 psia.

The instant invention also includes methods for forming azeotropic or azeotrope-like compositions of 1,1,1,2,3,3-hexafluoropropane, hexafluoropropane, and hydrogen fluoride by adding effective amounts of hydrogen fluoride and, optionally, hexafluoropropene to a solution of 1,1,1,2,3,3-hexafluoropropane. Properties associated with such an azeotropic mixture may be used to separate or distill 1,1,1,2,3,3-hexafluoropropane from a solution containing 1,1,1,2,3,3- hexafluoropropane and at least one impurity. In one embodiment, the impurity is a halocarbon such as, but not limited to, 1,1,1,2,3-pentafluoropropane, 1,1,1,3,3-pentafluoropropane, 1,1,1,2-tetrafluoropropane, 1,1,1,3-tetrafluoropropane, (E)1,2,3,3,3-pentafluoropropene, (Z)1,2,3,3,3-pentafluoropropene, 3,3,3-trifluoropropene, 1,1,1-trifluoropropane, 3,3,3-trifluoropropyne, (Z)1,3,3,3-tetrafluoropropene, and (E)1,3,3,3-tetrafluoropropene. In another embodiment, the impurities may or may not be miscible with 1,1,1,2,3,3-hexafluoropropane and may or may not form an azeotropic mixtures with 1,1,1,2,3,3-hexafluoropropane, hexafluoropropene, hydrogen fluoride or mixtures thereof.

The instant invention also relates to methods for isolating 1,1,1,2,3,3-hexafluoropropane from an azeotropic mixture containing 1,1,1,2,3,3-hexafluoropropane, hexafluoropropene, and hydrogen fluoride. Such a method includes, first, extracting hydrogen fluoride from a solution containing an azeotrope of 1,1,1,2,3,3-hexafluoropropane, hexafluoropropene, and hydrogen fluoride by contacting the mixture with a solution selected from an HF solvent, an HF absorbent, a basic solution and combinations thereof. Such HF solvents and/or HF absorbents are selected from sulfuric acid, water, potassium fluoride, sodium fluoride, alumina, zeolites, molecular sieves, silica gel, and combinations thereof. Next, 1,1,1,2,3,3-hexafluoropropane is separated from the remaining solution of 1,1,1,2,3,3-hexafluoropropane and hexafluoropropene. A preferred, though non-limiting, separation method includes distillation.

Additional embodiments and advantages to the instant invention will be readily apparent to one of ordinary skill in the art, based on the disclosure herein.

DETAILED DESCRIPTION OF THE INVENTION

In one embodiment, the instant invention relates to ternary azeotrope-like mixtures of 1,1,1,2,3,3-hexafluoropropane (HFC-236ea), hexafluoropropene (HFP) and hydrogen fluoride (HF). Such compositions may be used to isolate HFC-236ea from other impurities. The azeotrope-like mixture may then be separated into its component parts and HFC-236ea purified for further processing. In alternative embodiments, as provided in greater detail below, the instant azeotrope also exhibits use as nonaqueous etchant mixture, particularly for etching semiconductors in the electronics industry, as well as removing surface oxidation from metals.

For purposes of this invention, azeotrope or azeotrope-like mixtures of HFC-236ea, HFP, and HF, include those compositions or mixtures that behave like azeotropes. The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling. For the purpose of this invention, azeotropic compositions are defined to include azeotrope-like compositions which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree. Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

In one embodiment, the present invention provides a composition which includes an effective amount of HFC-236ea, HFP and HF to form an azeotropic or azeotrope-like composition. As used herein, "an effective amount" means an amount of each component that, upon combination with the other components, results in the formation of an azeotrope-like composition. More specifically, in non-limiting embodiments, the azeotrope-like composition of the present invention contains from about 1 to about 10 wt % HF, from about 1 to about 10 wt % HFP, and from about 80 to about 98 wt % of HFC-236ea, each based on the total weight of the azeotropic or azeotrope-like composition. In further embodiments, the azeotrope-like composition of the present invention contains from about 1.5 to about 8.4 wt % HF, from about 3.5 to about 4.9 wt % HFP, and from about 88.1 to about 93.6 wt % of HFC-236ea, each based on the total weight of the azeotropic or azeotrope-like composition. The composition has a boiling point of about from 0° C. to about 60° C. at a pressure of about 17 psia to about 125 psia.

In certain embodiments of the composition, 1,1,1,2,3,3-hexafluoropropane is present in an amount of about 80 to about 98 weight percent; hexafluoropropene is present in an amount of about 1 to about 10 weight percent; and hydrogen fluoride is present in an amount of about 1 to about 10 weight percent, based on the total weight of the azeotrope-like composition, provided that the azeotrope-like composition has a boiling point of about 0° C. at a pressure of about 17±3 psia.

In certain embodiments of the composition, 1,1,1,2,3,3-hexafluoropropane is present in an amount of about 80 to about 98 weight percent; hexafluoropropene is present in an amount of about 1 to about 10 weight percent; and hydrogen fluoride is present in an amount of about 1.5 to about 10 weight percent, based on the total weight of the azeotrope-like composition, provided that the azeotrope-like composition has a boiling point of about 25° C. at a pressure of about 44±5 psia.

In certain embodiments of the composition, 1,1,1,2,3,3-hexafluoropropane is present in an amount of about 80 to about 98 weight percent; hexafluoropropene is present in an amount of about 1 to about 10 weight percent; and hydrogen fluoride is present in an amount of about 2 to about 10 weight percent, based on the total weight of the azeotrope-like composition, provided that the azeotrope-like composition has a boiling point of about 60° C. at a pressure of about 123±5 psia.

The azeotrope-like compositions of the present invention may further include a variety of optional process components including, but not limited to, catalysts, reaction by-products, process starting materials, and the like. Preferably, though not exclusively, these optional process components do not affect the basic azeotrope-like characteristics of the composition.

Methods of the instant invention include the steps for generating the HFC-236ea/HFC/HF azeotrope and for isolating the azeotrope from impurities. HFC-236ea may be produced using one or more methods that are known in the art. In one non-limiting example, it may be produced as an intermediate in the production of 2,3,3,3-tetrafluoropropene (HFO-1234yf) which is well known in the art as described in US Application No. 20090234165, the contents of which are incorporated herein by reference. More specifically, HFC-236ea may be produced by the initial hydrogenation of a hexafluoropropene (HFP) under conditions effective to produce HFC-236ea or a mixture of HFP, HFC-236ea, and optionally co-products and unreacted starting materials. Each component can be purchased commercially and/or can be produced by methods known in the art.

The first step in removing HFC-236ea from this mixture, or any similar mixture containing HFC-236ea and an impurity, is by adding HF and HFP, as necessary, in effective amounts to form the foregoing azeotropic composition. Any of a wide variety of methods known in the art for combining three or more components to form a composition can be adapted for use in the present methods to produce an azeotrope-like composition. For example, HFC-236ea, HFP, and HF can be mixed, blended, or otherwise contacted manually and/or by machine, as part of a batch or continuous reaction and/or process, or via combinations of two or more such steps. In view of the disclosure herein, those of skill in the art will be readily able to prepare azeotrope-like compositions according to the present invention without undue experimentation.

Azeotropic-mixtures of the instant invention may be separated from other reaction impurities (e.g. catalysts, reaction by-products, process starting materials, and the like) using standard separation techniques, such as, but not limited to, swing distillation, extractive distillation, scrubbing, or other art recognized separating means. In one embodiment, the impurity itself does not form an azeotropic mixture with HFC-236ea, HFP, HF or any mixture thereof. In another embodiment, the impurity does form an azeotropic mixture with HFC-236ea, HFP, HF or any mixture thereof. Typical impurities of the process for producing HFC-236ea include, but are not limited to, other halocarbons which may be miscible with HFC-236ea such as, but not limited to, 1,1,1,2,3-pentafluoropropane, 1,1,1,3,3-pentafluoropropane, 1,1,1,2-tetrafluoropropane, 1,1,1,3-tetrafluoropropane, (E)1,2,3,3,3-pentafluoropropene, (Z)1,2,3,3,3-pentafluoropropene, 3,3,3-trifluoropropene, 1,1,1-trifluoropropane, 3,3,3-trifluoropropyne, (Z)1,3,3,3-tetrafluoropropene, and (E)1,3,3,3-tetrafluoropropene. The instant invention, however, is not limited to such impurities and may include other catalysts, reaction by-products, process starting materials, and the like, which are known or otherwise used for the purpose of producing HFC-236ea.

It also may be desirable to separate component parts of the HFC-236ea/HFP/HF azeotrope to a purified form HFC-236ea, for example, for further processing into other compounds, such as HFO-1234yf. Accordingly, the instant invention also relates to methods for separating component parts of the HFC-236ea/HFP/HF azeotrope, particularly after it is isolated from other impurities. Separation methods may include any method generally known in the art.

In one embodiment, for example, HF may be removed from the mixture by contacting or scrubbing the solution with an organic solvent or caustic solution. Organic solutions may include HF solvents, HF absorbents, basic solutions and combinations thereof. In one embodiment, HF solvents and HF absorbents are selected from sulfuric acid, water, potassium fluoride, sodium fluoride, alumina, zeolites, molecular sieves, silica gel, and combinations thereof. In preferred embodiments, though non-limiting embodiments, the organic solvent includes sulfuric acid alone or in combination with water and/or a basic solution. Post-extraction, a mixture of HFC-236ea and HFP remains. The HFC-236ea can then be separated from this mixture by conventional means known in the art, such as distillation or otherwise using extraction media having a high solubility for HFC-236ea and a low solubility for HFP. In addition to the foregoing, otherwise known extraction or separation methods for azeotropes may be adapted to separate or otherwise purify each component part.

Alternatively, the azeotropic and azeotrope-like compositions of the instant invention may also be used as nonaqueous etchant mixtures for etching semiconductors in the electronics industry, as well as compositions for removing surface oxidation from metals.

The following non-limiting examples serve to illustrate the invention.

EXAMPLES

Example 1

The normal boiling point of HFP, 236ea and HF are −29.6, 6.3 and 19.5° C., respectively. A mixture of 4.9 wt % 236ea, 93.6 wt % HFP and 1.5 wt % HF is made by combining 0.99, 19.06 and 0.31 gm of HFP, 236ea and HF, respectively. The pressure of the mixture was measured at 0, 25 and 60° C. as shown in table 1. An additional amount of high boiling (low pressure) component, HF, is then added to the mixture. The pressures are then re-measured and 0, 25 and 60° C. and show an increase in pressure. The increase in pressure indicates the existence of an azeotrope.

TABLE 1

PTx Data for a Ternary Mixture of HFP, 236ea and HF

| Wt % | | | Temp, | Press, |
|---|---|---|---|---|
| HFP | 236ea | HF | ° C. | psia |
| 4.9 | 93.6 | 1.5 | 0.0 | 17.5 |
| 4.9 | 93.6 | 1.5 | 24.9 | 42.7 |
| 4.9 | 93.6 | 1.5 | 59.8 | 112.7 |
| 3.5 | 88.1 | 8.4 | 0.0 | 17.8 |
| 3.5 | 88.1 | 8.4 | 24.9 | 44.2 |
| 3.5 | 88.1 | 8.4 | 59.8 | 123.0 |

Example 2

Using the data in example #1 and data available for HF/HFP (U.S. Pat. No. 6,407,297) and HF/236ea (U.S. Pat. No. 6,388,147) that data shown in Table 2 have been calculated. The data in Table 2 start with 4.9 gm of HFP and 93.6 gm of 236ea and incrementally add HF. Initially the overall pressure is seen to rise and then levels out after ~1 wt % HF has been added. The pressure then changes only slightly over the azeotrope-like region.

TABLE 2

Incremental addition of HF to a mixture of HFP and 236ea

| Wt, gm | | | Temp, | Press, |
|---|---|---|---|---|
| HFP | 236ea | HF | °C. | psia |
| 4.9 | 93.6 | 0.1 | 0.0 | 13.7 |
| 4.9 | 93.6 | 0.1 | 24.9 | 34.4 |
| 4.9 | 93.6 | 0.1 | 59.8 | 96.6 |
| 4.9 | 93.6 | 0.5 | 0.0 | 15.5 |
| 4.9 | 93.6 | 0.5 | 24.9 | 38.3 |
| 4.9 | 93.6 | 0.5 | 59.8 | 106.3 |
| 4.9 | 93.6 | 1.5 | 0.0 | 17.1 |
| 4.9 | 93.6 | 1.5 | 24.9 | 42.2 |
| 4.9 | 93.6 | 1.5 | 59.8 | 117.0 |
| 4.9 | 93.6 | 3 | 0.0 | 17.7 |
| 4.9 | 93.6 | 3 | 24.9 | 43.8 |
| 4.9 | 93.6 | 3 | 59.8 | 121.9 |
| 4.9 | 93.6 | 4.5 | 0.0 | 17.8 |
| 4.9 | 93.6 | 4.5 | 24.9 | 44.2 |
| 4.9 | 93.6 | 4.5 | 59.8 | 123.3 |
| 4.9 | 93.6 | 6 | 0.0 | 17.9 |
| 4.9 | 93.6 | 6 | 24.9 | 44.3 |
| 4.9 | 93.6 | 6 | 59.8 | 123.8 |
| 4.9 | 93.6 | 10 | 0.0 | 17.9 |
| 4.9 | 93.6 | 10 | 24.9 | 44.4 |
| 4.9 | 93.6 | 10 | 59.8 | 124.0 |

Example 3

The final mixture in example #1 which contained 3.5 wt % 236ea, 88.1 wt % HFP and 8.4 wt % HF was placed in a bath which was maintained at 25° C. A vapor sample was taken and the HF concentration was measured to be 7.7 wt %. This indicates that the azeotropic point contains ~8 wt % HF.

We claim:

1. A method for removing 1,1,1,2,3,3-hexafluoropropane from a mixture containing 1,1,1,2,3,3-hexafluoropropane and at least one impurity, comprising adding hydrogen fluoride and, optionally, hexafluoropropene to the mixture in an effective amount to form an azeotropic or azeotrope-like composition of 1,1,1,2,3,3-hexafluoropropane, hexafluoropropene, and hydrogen fluoride, and separating the azeotropic composition from the impurity.

2. The method of claim 1 wherein the impurity does not form an azeotropic mixture with 1,1,1,2,3,3-hexafluoropropane, hexafluoropropene, hydrogen fluoride or a mixture thereof.

3. The method of claim 1 wherein the impurity does form an azeotropic mixture with 1,1,1,2,3,3-hexafluoropropane, hexafluoropropene, hydrogen fluoride or a mixture thereof.

4. The method of claim 1 wherein the impurity comprises a halocarbon.

5. The method of claim 1 wherein the impurity is miscible with 1,1,1,2,3,3-hexafluoropropane.

6. The method of claim 1 wherein the impurity is selected from the group consisting of 1,1,1,2,3-pentafluoropropane, 1,1,1,3,3-pentafluoropropane, 1,1,1,2-tetrafluoropropane, 1,1,1,3-tetrafluoropropane, (E)1,2,3,3,3-pentafluoropropene, (Z)1,2,3,3,3-pentafluoropropene, 3,3,3-trifluoropropene, 1,1,1-trifluoropropane, 3,3,3-trifluoropropyne, (Z)1,3,3,3-tetrafluoropropene, and (E)1,3,3,3-tetrafluoropropene.

7. The method of claim 1 wherein the step of separating the azeotropic composition from the impurity is conducted by swing distillation or extractive distillation.

8. The method of claim 1 wherein the azeotropic composition consists essentially of about 1 to about 10 wt % hydrogen fluoride, from about 1 to about 10 wt % hexafluoropropene, and from about 80 to about 98 wt % of 1,1,1,2,3,3-hexafluoropropane, based on the total weight of the azeotropic or azeotrope-like composition and has a boiling point of about from 0° C. to about 60° C. at a pressure of about 17 psia to about 125 psia.

9. A method for isolating 1,1,1,2,3,3-hexafluoropropane from an azeotropic mixture containing 1,1,1,2,3,3-hexafluoropropane, hexafluoropropene, and hydrogen fluoride, comprising extracting hydrogen fluoride from a solution containing an azeotrope of 1,1,1,2,3,3-hexafluoropropane, hexafluoropropene, and hydrogen fluoride by contacting the mixture with a solution selected from the group consisting of an HF solvent, an HF absorbent, a basic solution and combinations thereof; and separating 1,1,1,2,3,3-hexafluoropropane from a remaining solution of 1,1,1,2,3,3 hexafluoropropane and hexafluoropropene.

10. The method of claim 9 wherein the HF solvent and HF absorbent are selected from the group consisting of sulfuric acid, water, potassium fluoride, sodium fluoride, alumina, zeolites, molecular sieves, silica gel, and combinations thereof.

11. The method of claim 9 wherein the separation of hexafluoropropene is by distillation.

* * * * *